(12) United States Patent
Seguin et al.

(10) Patent No.: US 6,172,250 B1
(45) Date of Patent: Jan. 9, 2001

(54) PREPARATION PROCESS OF BIOLOGICALLY ACTIVE SILICON COMPOUNDS IN A CONCENTRATED FORM

(75) Inventors: Marie-Christine Seguin; Jean Gueyne, both of Monaco (MC); Jean-Francois Nicolay, Villefranche-sur-mer; Andre Franco, Menton, both of (FR)

(73) Assignee: Exsymol S.A.M., Monaco (MC)

( * ) Notice: Under 35 U.S.C. 154(b), the term of this patent shall be extended for 0 days.

(21) Appl. No.: 08/647,907

(22) PCT Filed: Sep. 29, 1995

(86) PCT No.: PCT/FR95/01267

§ 371 Date: Jul. 16, 1996

§ 102(e) Date: Jul. 16, 1996

(87) PCT Pub. No.: WO96/10574

PCT Pub. Date: Apr. 11, 1996

(30) Foreign Application Priority Data

Sep. 30, 1994 (FR) .................................................. 94 12089

(51) Int. Cl.$^7$ .................................. C07F 7/08; C07F 7/10
(52) U.S. Cl. .......................... 556/407; 556/408; 556/409; 556/410; 556/411; 556/466; 556/413; 556/419; 556/418; 556/426; 556/460; 556/461; 514/64; 514/844; 514/944; 424/401; 424/457; 424/78.03; 424/48; 424/49; 424/70.1; 424/78.04; 549/214
(58) Field of Search ..................................... 556/466, 408, 556/410, 407, 411, 409, 413, 460, 418, 461, 419, 426; 514/64, 844, 944; 424/401, 457, 78.03

(56) References Cited

U.S. PATENT DOCUMENTS 5,648,511 * 7/1997 Ng et al. .......................... 556/410 X

\* cited by examiner

Primary Examiner—Paul F. Shaver
(74) Attorney, Agent, or Firm—James C. Lydon

(57) ABSTRACT

A process for the preparation of biologically active silicon compounds by hydrolysis of a precursor which produces a compound which prevents the formation of polymers from the silicon hydrolyzed bonds.

21 Claims, No Drawings

PREPARATION PROCESS OF BIOLOGICALLY ACTIVE SILICON COMPOUNDS IN A CONCENTRATED FORM

SUMMARY

Preparation process of a biologically active compound consisting in hydrolyzing a precursor with the formula

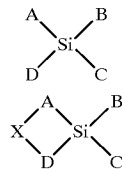

in which A, B, C, D and X indicate radicals different from OH, the A B, C, D bonds with the Si atom being covalent bonds and 2 or 3 of these bonds are hydrolysable. The hydrolysis is carried out in a solvent containing a small quantity of water in a proportion with regard to the solvent preferably included between 0.1% and 5%, and at least one of the compounds obtained from the silicon hydrolyzed bonds is a compound said stabilizing preventing the formation of polymers from silicon hydrolyzed bonds.

TECHNICAL FIELD

The present invention concerns biologically active silicon compounds and in particular a process for the preparation of biologically active silicon compounds in a concentrated form starting from hydrolysable precursors.

BACKGROUND ART

Silicon is a very common element in nature and is generally known under its natural inorganic forms such as silica and silicate, and also under the form of synthetic polymers, the silicones. These silicon-containing compounds are barely soluble or not at all soluble in aqueous medium which explains their weak incidence at the alive organisms level. The silicones, in particular, are characterized by a great inertia towards the biological medium and consequently present a high biocompatibility.

However, the silicon, even in minute quantities, plays an important biological role and must be considered as an essential element of life. It is especially necessary for a normal growth of numerous species. It has been demonstrated that silicon was intervening in the connective tissue structuration in interacting with the glycosaminoglycan and proteins. This is one of the constitutive elements of proteins-glycosaminoglycan complexes found in the extracellular matrix of these tissues. Silicon also interacts with the glycosaminoglycan in the cartilage tissue development. We also know that silicon plays an important role in the bone formation where it favours the mineralization process.

Besides, silicon can be considered as a collagen constituent and we think that it plays a major role in the reticulation process of collagen fibers. Silicon also intervenes at the hair texture level where it would especially contribute to increase the resistance of the hair fibre. Silicon is also involved in the cell metabolism and it would be especially favourable to the metabolic activity of osteoblasts.

Beyond the cross-linking power of silicon and its implication in the metabolic activity of some cells, it appears that a high silicon content, in the tissues, jointly with the glycosaminoglycan content is characteristic of healthy and metabolically active tissues. In the same way, numerous works have demonstrated the importance of silicon in the physiological cycle regulation of the hair.

Today's researches tend to reinforce the idea that silicon intervenes in numerous biological mechanisms. Recent works have even demonstrated that silicon plays a major role in the aluminum elimination by biological systems.

Works of the applicant have demonstrated that silicon compounds could constitute a form of assimilable silicon by the organism (as opposed to mineral silicon or to silicones) on condition that it possesses the characteristic of existing in aqueous solution under the form of soluble oligomers of low molecular weight. Furthermore, another necessary characteristic of the oligomers activity in aqueous solution is to present numerous Si—OH functions. So, it is evident that the biological properties of these bioavailable compounds are only observed if they form soluble oligomers in aqueous solution, which result from a chain of siloxane bonds Si—O—Si, rich in Si—OH functions.

Apart from the fact that the presence of Si-OH highly polar functions confers their water solubility to the oligomers, at the present time, we think that a part of the properties observed are conducted by the fact that the chemical species involved in most of the above mentioned biological mechanisms would be a form of soluble silicon, the silicic acid of $Si(OH)_4$ formula. This compound only exists at very low concentrations in water since it has a very strong tendency to polycondense to form silica.

Consequently we have researched more stable products similar to silicic acid, by chemically modifying the Si-OH functions. It quickly became obvious that these functions were essential for the biological activity. In other respects, we knew that a series of natural compounds, and among them, the tannins and the catecholamines were capable of forming a complex with the silicic acid and like this were capable of increasing its stability in solution. These complexes would be the way of transport for the silicic acid in the organism and it is under this form that the cell would introduce the silicon. Nevertheless, their stability is still too weak for the carrying out of a pharmacologically active product.

The applicant has perfected active analogues of these complexes. It concerns products resulting from the complexation between a complexing molecule and an active organo-silicon compound. The characteristic of these compounds is to possess several Si-OH functions like the silicic acid, but also one or two carbon-silicon bonds. Nevertheless, these analogues possessing researched biological properties, even if they are more stable than the silicic acid complexes, still they must be prepared under the form of diluted aqueous solutions, which silicon content cannot exceed 2 g/litre owing to the fact that with a higher concentration, we would favour the polycondensation.

SUMMARY OF THE INVENTION

This is why the main goal of the invention is to provide biologically active silicon-containing compounds not developing towards the formation of inactive polycondensed forms such as polysiloxane.

Another goal of the invention is to carry out a preparation process of biologically active silicon compounds under a concentrated form by hydrolysis of silicon containing precursors with the release of stabilizing products preventing the polycondensation of silicon compounds.

The subject of this invention is then a preparation process of a biologically active silicon compound consisting in hydrolyzing a precursor having the formula

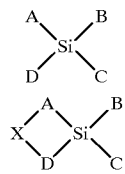

in which

A, B, C, D and X indicate radicals different from OH, the links A, B, C, D with the Si atom being covalent bonds and 2 or 3 of these bonds are hydrolysable. The hydrolysis is carried out in a solvent containing a small water quantity and in a proportion with regard to the solvent preferably between 0.1% and 5%, and at least one of these compounds coming from the hydrolyzed bonds of silicon is a compound said stabilizing preventing the formation of polymers from the silicon hydrolyzed bonds.

DESCRIPTION OF THE INVENTION

All along the description, we shall call "silyl" the biologically active compound obtained from the invention process, keeping the word "precursor" to indicate the biologically inactive silicon compound, and which is hydrolysable according to the invention process.

Radicals which are hydrolysable are either hydrogen atoms or preferably radicals linked to Si by an oxygen atom, a nitrogen atom or by a sulphur atom. Therefore, they can be esters or alkoxy, aryloxy radicals such as phenoxy radicals or allyloxy or vinyloxy radicals, when the silicon atom is directly bond to an oxygen atom. These radicals can also be thioester or aryl or alkylthioether radicals, when the silicon is bound by a sulphur atom. The radicals can also be amines, mono or disubstituted by hydrocarbon chains substituted or not by one or several functional groups, aryl or alkylamide, when the silicon is bound to a nitrogen atom.

The radicals bound to Si and which are not hydrolysable can be hydrocarbon radicals, substituted or not by one or several functional groups, certain alkoxy radicals with a steric hindrance, the fluorocarbon radicals or even a fluorine atom.

In the second type of general formula, the radical X can be an hydrocarbon radical, substituted by one or several functional groups, bound to silicon (bond A or B) by at the best one nonhydrolysable bond.

An important characteristic of the process according to the invention is that the precursor hydrolysis occurs in "gentle" conditions that is to say at neutral pH and without any chemical or enzymatic catalyst. The precursor is hydrolyzed in a solvent containing 0.1% to 5% of water compared with the whole. Preferably, the precursor is added to a solvent (containing water) drop by drop, under shaking, stirring steadily the temperature. The solvent can be an alcohol such as ethyl alcohol, isopropanol or a fatty alcohol such as cyclohexanol or octyldodecanol, a glycol such as propylene glycol, butylene glycol, the hexylene glycol or polyethylene-glycol (ex: PEG 400) or even a water miscible organic solvent such as the acetone or ethyl acetate. When hydrolysis releases an acid, it is well-advised to add a stoichiometric quantity of a base compatible with the solvent used, such as the triethanolamine in order to neutralize the acid formed during the hydrolysis. When the hydrolysis releases a base, it can be better to add a stoichiometric quantity of an acid. The suitable acids are preferably carboxylic acids, and in particular the acetic acid or the lactic acid.

An alternative to the above method consists in solubilizing first the precursor in an oily medium containing a small quantity of water as defined previously. Afterwards, we add an small quantity of an alcohol or a oil-miscible glycol. The composition obtained can be used to form an emulsion.

Another essential characteristic is that the silicon atom is bound by at least one hydrolysable bond to a compound which is stabilizing. After hydrolysis, when the precursor is according to the first type of general formula, the stabilizing agent is released in the medium and stabilizes the silyl by forming weak bonds with it (hydrogen bonds) and prevents the polycondensation.

The stabilizing power of these agents can also be explained by their ability to reform a transitory covalent bond. We then obtain a dynamic structure where some bonds possess a "mixed character" (hydrogen bonds, covalent bonds). For sure, when the precursor is according to the second type of general formula, the stabilizer can remain bound to the silyl by a covalent bond.

The stabilizers complying with the above stated criterion, are after hydrolysis, hydroxy carboxylic acids compounds and especially alpha and beta hydroxyacids, the glucuronides, hydroxylated or phenolic amino acids such as serine, threonine or tyrosine, compounds possessing several alcohol (or phenol) functions and above all vicinal alcohol (or phenol) functions. We can quote in this category, glycol, catechol and catecholamine (DOPA, adrenalin), polyethyleneglycol, polyol as glycerol, monosaccharides (L-threose-, L-ribose, sorbitol . . . ); phenolic acids such as gallic acid, 3,4-dihydroxybenzoic acid or caffeic acid, and esterified derivatives; diacides such as malonic acid ; some compounds possessing a particular geometry adapted to stabilize the silyl complexes in aqueous medium, as the tropolones (ex: thujaplicine).

Examples of precursors being used in the process according to the invention are given here under Amino-acids derivatives:

Dimethylsilyl-N-acetylcysteine
Stabilizer: cysteine

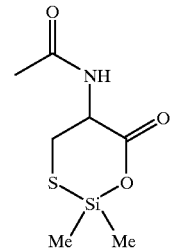

Dimethylsilyl-L-methionine
Stabilizer: methionine

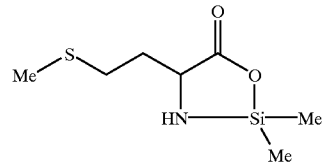

-continued

Dimethylsilyl-L-serine
Stabilizer: serine

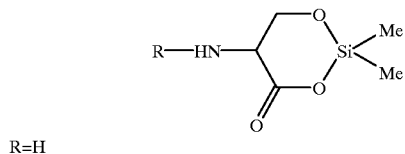

R=H

Salicyclic acids derivatives 2,2-ethoxymethyl-4-oxobenzo-1,3-dioxa-2-silane
Stabilizer: salicylic acid

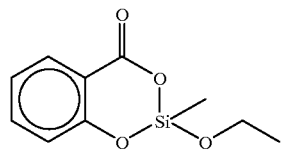

2,2-dimethyl-4-oxobenzo-1,3-dioxa-2-silane
Stabilizer: salicylic acid

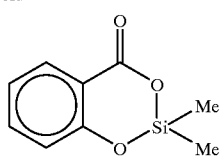

2,2-ethoxy,n-octyl-4-oxobenzo-1,3-dioxa-2-silane
Stabilizer: salicylic acid

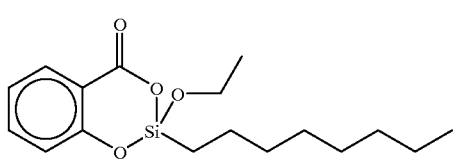

Miscellaneous 1,2-3,4-5,6-ethoxymethylsilyl-sorbitol or
tri (ethoxymethylsililyl) sorbitol
Stabilizer: sorbitol

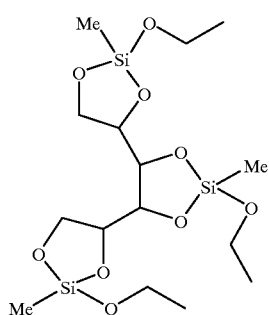

2,3-dimethyldilyloxy-N-(3-hydroxypropyl)-3,3-butanamide or
dimethylsilylpantothenol:
Stabilizer: panthenol

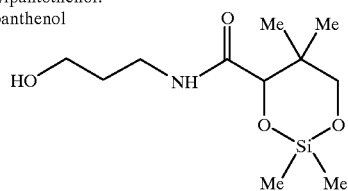

-continued

Bis-dimethylsilyl-ascorbate:
Stabilizer: ascorbic acid

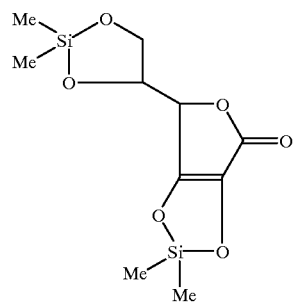

2,2-ethoxymethyl-4-oxo-5-methyl-1,3,dioxa-2-cyclosilane:
Stabilizer: lactic acid

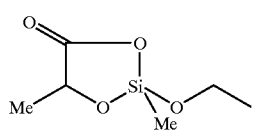

Caproyl-diethoxymethylsilane
Stabilizer: caproic acid

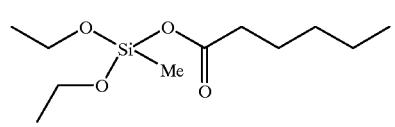

Generally speaking the compounds according to the invention will be able to be used in numerous applications requiring the properties of the "silyl" forms, that is to say the therapeutic, dietetic or cosmetic properties resulting from the anti-inflammatory, regenerating, anti-degeneration, normalizer, metabolic stimulator, anti-free radical and anti-glycation, and again generally speaking, for the stimulating activity of the organism defences.

The interest of the products obtained according to the invention is that they present a high concentration in silyl. Whereas the strongest concentration being possible to be obtained with the standard methods, without risking the polycondensation, is of 2 g per litre of water, it is possible to obtain, using the process of the invention a silyl concentration going up to 50 g per kg of solvent.

The concentrated solution of silyl can be prepared by using various solvents, which offers a large flexibility for their formulation. They can lead to different formulations of aqueous or semi-aqueous type such as lotions, eye-drops, mouth-wash lotions, creams, gels, tooth-pastes, chewing-gums etc . . . . The oily silyl concentrates are preferably used for emulsions or creams preparations. When the concentrated silyls are prepared in a solvent relatively volatile (acetone, ethanol), it is possible, after formulation in a less volatile solvent (such as water) to eliminate the solvent of origin of the silyl. This is generally carried out by evaporation under reduced pressure.

The following examples are illustrative (but not restrictive) of the formulations used as medicine or cosmetic products in order to demonstrate the above stated activities.

EXAMPLE 1

Regenerating activity

Restructuration of the capillary coats

In this example, the hydrolyzed precursor according to the invention process is caproyl diethoxymethylsilane, M.M.=248.39 (SiOH=19%) which is equivalent to a Si concentration equal to 30 g/kg.

As from the obtained silyl, we formulate a Carbopol aqueous gel protected by propyl- and methyl-paraben (we eliminate the starting solvent by evaporation under reduced pressure). We obtain then a formulation with a high concentration of active constituent equal to 5.3%.

This gel has been tested on lymphoedema of the upper limb by sequential pressotherapy and lymphatic drainage on 62 patients by massage-kinesitherapists.

The results given in terms of reduction of the oedema volume have been the following:

| Number of patients | Reduction |
|---|---|
| 3 | <10% |
| 13 | from 10 to 25% |
| 29 | from 25 to 50% |
| 13 | from 50 to 75% |
| 2 | from 75% to 100% |
| 2 | ≧100% |

Which gives an average reduction of 45%

EXAMPLE 2

Anti-glycation activity

Anti-cataract lotion

The original precursor for the chosen eye-drop is the dimethyl-silyl-N-acetyl-cysteine having as formula $C_7H_{13}NO_3SSi$, M.M.=219.33 corresponding to 21% of SiOH or 12.7% of Si following gentle hydrolysis with ethanol.

We have formulated a sterile solution (we eliminate the ethanol under reduced pressure), degasified, protected by methylparaben with 0.4% of silyl.

Such eye-drop is used for lenses with abnormal transparency especially for the opacities of senile origin.

It is interesting to prevent senile cataract in resisting against the glycation phenomena as it is demonstrated by the in-vitro test.

The non enzymatic glycosylation of proteins is one of the factor responsible for the sclerosis of the connective tissues. The chemical reactions involved in the proteins degradation have been identified. The glycation (non enzymatic glycosylation) between sugar and proteins is carried out at random of the free aminated proteic sites and form betaketomethylamines bonds (Amadori product). These latter start a series of chemical reactions which result in a progressive increase of the proteins reticulation. Those irreversible links progressively induce the lost of the properties (elasticity) of the supporting tissues, which explains their sclerosis.

We have perfected an original experimental procedure that allowed us to study in vitro the silyl specific reactivity in the proteic glycation phenomenon.

The degree of glycosylation can be evaluated by a calorimetric method specific for the dosage of the glucose-protein formation. This technique allows to demonstrate the 5-hydroxymethyl-furfural (HMF) released from the carbohydrate after an acid hydrolysis. The HMF ratio is quantitatively determined by the calorimetric reaction with the 2-thiobarbituric acid (TBA).

As a result, the protein (albumin) cross-linking ratio has been reduced in a significant way (−37%) when, for the in-vitro test, the dimethyl-silyl-cysteine is added to the proteic solution at the beginning of the reaction. This experimentation confirms the very perceptible anti-glycation biological role of the silyl obtained by controlled hydrolysis of the dimethyl-silyl-N-acetyl-cysteine.

EXAMPLE 3

Anti-inflammatory hydrating regenerating activity

Dermo-pharmaceutical composition

In this example, we have used as a precursor the 2,2-ethoxy-n-octyl-4-oxobenzo-1,3-dioxa-2-silane having the formula $C_{17}H_{26}O_4Si$ of M.M.=322.48 corresponding to 14% of SiOH after hydrolysis. We use the resulting concentrated solution in stearyloctanoate added with ethanol.

The n-octyl-silyl-salycilate obtained is a cosmetodermopharmaceutical indicated for deprived skins or skins affected by the sun, the wind, the acnea . . . .

The test were performed with an astringent, regenerating, anti-inflammatory, hydrating lotion.

| | |
|---|---|
| Zinc Sulfocarbonate | 3.00 |
| Stearyl octanoate | 8.00 |
| n-octyl-silyl-salicylate | 3.50 |
| Ethyl alcohol | 20.00 |
| Demineralized water | 100.00 |

Considering the biological activity, we shall note that the fatty alcohols soften the keratin accumulates and that the released salicylic acid at the cutaneous level contributes to separate them. The SiOH function increases the action of the salicylic acid ensuring a penetration more important and normalizing the keratinocytes metabolism and their proliferation. The inflammation regresses with a proper healing of the pimples.

EXAMPLE 4

Anti-inflammatory action

Stomatologic therapy

For this composition, we have used as a precursor the 2,2-dimethyl-4-oxobenzo-1,3-dioxa-2-silane of formula $C_9H_{10}O_3Si$ and M.M.=194.26, which is equivalent to 24% of SiOH after hydrolysis, or the 2,2-ethoxymethyl-4-oxobenzo-1,3-dioxa-2-silane of formula $C_{10}H_{12}O_4$ Si and M.M.=224.26 which is equivalent to 21% SiOH after hydrolysis. The gentle hydrolysis is carried out in an appropriate solvent before formulation.

Several products of hygiene for the gums have been tested: mouth-wash, tooth-paste and chewing gum, and the freedom have been left to the persons involved in those tests. In more than 70% of the cases, we have observed an anti-inflammatory and regenerating action of the gums for all the group, and for two persons who kept using the gingival gel on the basis of 2 applications a day, for more than 6 months, we have seen a reduction of the shrinking of their gums; this pathology being associated with osteoporotic disorders.

The silyl-salicylate used in this example allows therefore to fight against the parodontal diseases reaching the supporting tissues of the teethes and to ensure that way a good calcification.

In all the cases, we have noted, when using these compounds, a reduction of the spontaneous bleedings when brushing and the reduction of the gingival sensitivity. In one case, we have noted the gingival re-covering of some teethes getting loose, and in three cases, we have noted a stabilization or a decrease of the shrinking.

| Gingival solution - mouth-wash | |
| --- | --- |
| Silyl-salicylate | 5.00 |
| Ethanol | 10.00 |
| Mint oil | 0.50 |
| Demineralized water q.s. | 100.00 |
| Gingival gel | |
| Carbopol | 0.20 |
| Silyl-salicylate | 5.00 |
| Ethanol | 10.00 |
| Mint oil | 0.80 |
| Demineralized water q.s. | 100.00 |
| Tooth-paste | |
| Silyl-salicylate | 4.00 |
| Unsoluble metaphosphate | 40.00 |
| Glycerine | 13.00 |
| Sorbitol at 70% | 19.00 |
| Sodium alginate | 2.00 |
| Sodium laurylsarcosinate | 2.00 |
| Titanium oxide | 0.95 |
| Mint essence | 0.80 |
| Demineralized water q.s. | 100.00 |
| Chewing gum | |
| Silyl-salicylate | 1.80 |
| Paste q.s. | 100.00 |

EXAMPLE 5

Metabolic stimulating action

Anti-hair loss composition

The compound used is the 2,3-dimethylsilyloxy-N-(3-hydroxypropyl)-3,3-butanamide of formula $C_{11}H_{23}NO_4$ and M.M.=261.39, which is equivalent to 18% of SiOH or 10.7% in Si.

The silyl-panthenol obtained after hydrolysis can be used either at a pure state or diluted in a mixture of butanediol and water 50:50 on the basis of 40% of pure product. This corresponds to a 4% concentration in Si, that is to say an important quantitative supply:

The formula of this hair lotion is the following:

| Silyl panthenol | 5.00g |
| --- | --- |
| Water/Butanediol 50/50 | 7.50g |
| Propylen glycol | 14.00g |
| Alcohol at 70° | 100.00g |

The lotion applied in daily rubbing has been tested on male seborrhoeic alopecia. 10 out of the 23 patients tested, were between 15 and 25 years old, 11 between 26 and 35 years old, 1 of 45 years old and 1 of 55 years old.

The reasons of the inclusion in the experimentation were in all the cases a hair loss considered as abnormal, determined by a seborrhoeic alopecia. In all the cases, we have noticed a sparseness of the hair which was visible and beyond doubt.

The results were the following:
Excellent results: 59%, good results: 9% average results: 18% and no results: 14%.

The results were confirmed by the trichogram performed practically on a yearly basis, determining the ratio anagen/telogen. They have been as follows:

before the experimentation ratio A/T—frontal 2.8—occipital 1.5—temporal 4 after the experimentation ratio A/T—frontal 4.8—occipital 3.6—temporal 5

The average obtained for the best results (excellent+good), therefore have been of 70% of the treated patients.

EXAMPLE 6

Regenerating activity

Anti-wrinkles cosmetic composition

Different alpha-hydroxy-acids silyls derivatives have been formulated, -from dimethylsilyl-2-oxo-octanoate or ethoxymethylsilyl-2-oxo-octanoate or 2,2-ethoxymethyl-4-oxo-5-methyl-1,3-dioxa-2-cyclosilane precursors dissolved at 30% in 1,3-butanediol which corresponds to average and in solution, supplies of 8% in SiOH, (5% in Si).

It is also possible to use as precursors some derivatives of aminoacids such as the dimethyl-silyl-N-acetyl-cysteine (M.M.=219.33) at 60% in a solution of octyldodecanol, which corresponds to administration of 14% SiOH.

The different silyl obtained after hydrolysis have been used in different formula: cream, milk, gel, or lotion at doses from 5% to 10% which give supplies from 0.7% to 1.4% in SiOH.

So, we have carried out an aqueous gel containing 7.6% of silyl-2-hydroxycaprilate using the 1,3-butanediol (30:70) which corresponds to a supply of 0.50% of SiOH, that is to say 3 times the content of the same product obtained without the invention process. The gel has been daily applied at night on a perfectly clean skin.

The persons tested were women from 55 to 67 years old. We have observed a reduction of the small wrinkles and an attenuation of the deeper wrinkles. The skin was smoother, more tonic and brighter, as it has been verified by an in vitro test, on aged fibroblasts cell culture.

A cytostimulating activity experimentation has been conducted on monolayer cultures of keratinocytes and fibroblasts. The cell proliferation has been measured by a colorimetric neutral red assay. The analysis has been determined by UV spectrometry (540 nm). To simulate the conditions of a test with aged cells, the latter have been cultured in a depressing medium containing suboptimal concentrations of foetal calf serum (FCS).

Results: the cells growth has been increased in a significant way after enrichment of the culture medium by concentrated silyl solutions. The amplitude of the response to cytostimulation has been very important, especially on fibroblasts, cells involved in the collagen and elastin synthesis, which have express a very perceptible reaction. We have noticed a 200% stimulation of the kinetics of fibroblasts proliferation as compared to control-cultures with 2.5% FCS.

EXAMPLE 7

Normalizing action

Hydrating cosmetic composition

In this example, the chosen precursor has been the triethoxy-methylsilyl-sorbitol of formula $C_{15}H_{32}O_9Si_3$, M.M.=440.67, which is equivalent to 31% in SiOH (16% in Si) after hydrolysis.

With the silyl-sorbitol obtained, we have carried out a very fine hydrodispersible emulsion with a lipid content of 35%, the silyl-sorbitol being incorporated at 0.5%.

This emulsion has been used on dehydrated dry skins. Since the first applications, we have noted a superficial epidermic modification very perceptible by touching. There is a restoration of the hydrolipidic film at the epidermis/horny layer level.

An in vivo verification by Fourier Transformed I.R. spectrum, has demonstrated a biological hydratation by addition of bound water.

EXAMPLE 8

Anti-free radical activity

Daytime Cosmetic products colored or not

The precursor used has been the dimethyl-silyl-2,3,5,6-ascorbate with the formula $C_{10}H_{16}O_6Si_2$ Of M.M.=288.4 which is equivalent to 32% of SiOH (19.4% of Si) after hydrolysis.

In order to provide a protection to the face against oxidative phenomena, we have formulated a day cream hydrodispersible emulsion or foundation in which the silyl has been incorporated on the basis of 1%. Consequently, no modification was to be suspected at the products texture level, even though we had 0.3% of SiOH (0.19% of Si).

The anti-free radical activity of the formulation has been demonstrated in vitro by a test which consists in producing oxygenated free radicals by an enzymatic way (xanthine oxydase action on acetaldehyde) and in comparing the resistance of cells cultured with or without silyl when in contact with these free radicals.

The addition of the free radicals within a cell culture induces a cytotoxicity. This toxicity results in a cell lysis with an increase of the cell lactate deshydrogenase (LDH). The evaluation of the cell resistance to the radical stress is obtained by the LDH activity dosage by UV spectrophotometry.

We have observed a very noticeable effect of the formulation used. The peroxidative system used has produced superoxide ions and hydrogen peroxide. The study of the results show that the formulation induces a protection against the spontaneous cell lysis (LDH activity reduced of 67%). This protection persists and clearly intensifies itself (LDH reduction of 75%) in the presence of an induced radical stress.

What is claimed is:

1. A process for the preparation of a silyl biologically active compound, comprising hydrolyzing a precursor having the formula:

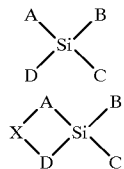

in which A, B, C, D and X indicate radicals different from OH, and the linkages of A, B, C, D with the Si atom are covalent bonds and 2 or 3 of these bonds are hydrolysable, wherein the hydrolysis is carried out in an aqueous solvent and at least one compound obtained is a stabilizing compound which prevents the formation of polymers from the silicon hydrolyzed bonds.

2. Process according to claim 1 performed at neutral pH and in the absence of any chemical or enzymatic catalyst and in which the said precursor is added drop by drop into the aqueous solvent under stirring.

3. Process according to claim 1 in which the said solvent is selected from the group consisting of alcohols and water miscible organic solvents.

4. Process according to claim 1 comprising first solubilizing the precursor in an oily compound containing water, and then adding an alcohol or a glycol miscible with the said oily compound thereto.

5. Process according to claim 1 in which at least one of the said radicals A, B, C, D of said precursor is bound to the silicon atom by an oxygen atom.

6. Process according to claim 5, in which at least one the said radicals A, B, C, D bound to the silicon atom is an ester moiety.

7. Process according to claim 1 in which at least one of the said radicals A, B, C, D is a phenoxy group.

8. Process according to claim 1 in which a stabilizing compound obtained is selected from the group consisting of hydroxy carboxylic acids, hydroxylated or phenolic aminoacids, glycols, catechol, catecholamine, polyols, monosaccharides, phenolic acids and esterified derivatives thereof.

9. A composition comprising a silyl obtained by the process according to claim 1 in combination with a carrier therefor.

10. A composition according to claim 9 in which the said precursor is caproyldiethoxymethylsilane, and the said composition contains the silyl in an amount sufficient to provide a regenerating activity for the re-structuration of capillaries.

11. A composition according to claim 10 in which the carrier comprises an aqueous gel.

12. A composition according to claim 9 in which the said precursor is dimethyl-silyl-N-acetyl-cysteine, and the composition contains an anti-glycation amount of the silyl for the treatment of cataracts.

13. A composition according to claim 12 in which the carrier is an eye-drop.

14. A composition according to claim 9 in which the precursor is 2,2-ethoxy-n-octyl-oxobenzo-1,3-dioxa-2-silane, and the composition contains an anti-inflammatory, hydrating, regenerating activity for the cutaneous pathologies treatment effective amount of the silyl.

15. A composition according to claim 9 in which the said precursor is 2,2-dimethyl-4-oxobenzo-1,3-dioxa-2-silane or 2,2-ethoxymethyl-4-oxobenzo-1,3-dioxa-2-silane, and the composition contains an anti-inflammatory effective amount of the silyl.

16. A composition according to claim 15, in which the carrier is a gingival solution, gingival gel, toothpaste or chewing gum.

17. A composition according to claim 9 in which the said precursor is 2,3-dimethysilyloxy-N-(3-hydroxypropyl)-3,3-butanamide, and the composition contains a metabolic stimulating activity for the hair loss treatment effective amount of the silyl.

18. A composition according to claim 17 in which the carrier is a hair lotion.

19. A composition according to claim 9 in which the said precursor is a derivative of a silyl alpha-hydroxy-acid selected from the group consisting of dimethysilyl-2-oxo-octanoate, ethoxymethylsilyl-2-oxo-octanoate, and 2,2-ethoxymethyl-4-oxo-5-methyl-1,3-dioxa-2-cyclosilane, the carrier is a cosmetic carrier and the composition contains a regenerating activity effective amount of the silyl for anti-wrinkles treatment.

20. A composition according to claim 9 in which the said precursor is tri-ethoxy-methylsilyl-sorbitol, and the composition contains a normalizing activity effective amount of the silyl for dry skin treatment.

21. A composition according to claim 9 in which the said precursor is dimethyl-silyl-2,3,5,6-ascorbate, the carrier is a cosmetic carrier and the composition contains an anti-free radical activity for the skin protection effective amount of the silyl.

* * * * *